United States Patent [19]

Liu

[11] Patent Number: 4,999,376

[45] Date of Patent: Mar. 12, 1991

[54] PHARMACEUTICAL COMPOSITION FOR TREATING AND PREVENTING CARDIOVASULAR DISEASE

[76] Inventor: Yaguang Liu, 30 Seaman Ave., New York, N.Y. 10034

[21] Appl. No.: 449,747

[22] Filed: Dec. 13, 1989

Related U.S. Application Data

[62] Division of Ser. No. 910,240, Sep. 22, 1986, Pat. No. 4,906,470.

[51] Int. Cl.$^5$ .................. A61K 31/335; A61K 31/045
[52] U.S. Cl. ..................................... 514/468; 514/738
[58] Field of Search .............................. 514/238, 468

[56] References Cited

PUBLICATIONS

Chemical Absts 95:14394q, 1981; 100: 188750r, 1984.
Chem Absts. 98: 122813m, 1983; 103: 19811g, 1985.
Chem Abst 95:145225c, 1981 and 111:12392c, 1989.
Chem. Abst. 109:79804r 1988.

Primary Examiner—John W. Rollins
Attorney, Agent, or Firm—Chewpatents

[57] ABSTRACT

The new pharamaceutical composition (PTC) and process are provided for treating and preventing cardiovascular disease.

The fine-PTC is composed of following ingredients: Puerarin or derivate of Puerarin; Danshensu or Danshenketone; Tetramethyl pyrazine; Polysaccharides and Ssponin of Dangshen.

The composition is nontoxic.

4 Claims, No Drawings

PHARMACEUTICAL COMPOSITION FOR TREATING AND PREVENTING CARDIOVASULAR DISEASE

This application is a division, of application Ser. No: 910,240, now U.S. Pat. No. 4,986,470, filed 09/22/86.

FIELD OF THE INVENTION

The present invention provides a pharmaceutical composition for treating and preventing cardiovascular disease and process for isolating it. The pharmaceutical composition is nontoxic.

DESCRIPTION OF THE PRIOR ART

Some drugs are used in treating cardiovascular disease, but all of them have a certain degree side-effects. For example, nitroglycerin and other organic nitrates are useful in the treatment of angina. The research results indicate that the relief of effort angina with nitrates is due primarily to decreased myocardial oxygen demand and not increased coronary blood flow. However, nitroglycerin and other organic nitrates have the following side-effects: throbbing headache, dizziness, weakness, orthostatic hypotension, tachycardia, or even syncope et al.

Propanolol has proved to be effective in hypertension and to reduce the frequency of anginal episodes and to improve exercise tolerance in patents with angina. Propanolol is a Beta-receptor antagonist which has some effects on the heart. The negative inotropic and chronotropic effects are predictable from the role of adrenergic receptors in regulating these functions. However, propranolol has some toxicity: because propranolol has properties of Beta 1 and Beta 2-receptor blockade.

Beta 2-receptor blockade associated with the use of nonselective agents commonly causes worse of preexisting asthama and other forms of airway obstruction. Indeed, some asthama may become severe after propranolol. Great caution must be exercised in using propranolol in patients with myocardial infarction or compensated congestive heart failure. A very small dose of propranolol (10 mg) may provoke severe cardiac failure in susceptible individual. Evidence suggests that patients with ischemic heart disease may be at increased risk if propranolol is suddenly interrupted. Propranolol may be at increased risk for patients with hyperthyroidism.

Calcium-antagonists occupy important position in cardiovascular drug. Cardiac muscle is highly dependent upon calcium influx for normal function. Impulse generation in the sinoatrial node and conduction in the atrioventricular node are blocked by all of the calcium influx inhibitors. Excitation-contraction coupling in all cardiac cells requires calcium influx, the calcium influx inhibitors may reduce the oxygen requirement in patients with angina.

But calcium antagonists have serial adverse side effects. For example, the most important toxic effects reported for the calcium influx blockers are direct extensions of their therapeutic action. Excessive inhibition of calcium influx can cause serious cardiac depression, including cardiac arrest, bradycardia, atrioventricular block, and congestive heart failure. Patients receiving Beta-adrenergic blocking drugs are more sensitive to the cardiodepressant effects of calcium influx inhibitors. Minor toxicity includes flushing, edema, dizziness, and nausea.

Dipyridamole (persantine) is a pyrimidopyrimidine compound that can increase coronary blood flow and inhibit some platelet functions. It inhibits phosphodiesterase activity, thereby increasing cAMP levels in the platelet. However, dipyridamole has following side-effects: dizziness, headache, weakness, nausea, diarrhoea et al.

Digitalis is the cardiac glycosides which comprise a group of steroid compounds. The therapeutic direct action of cardiac glycosides on mechanical function is to increase the intensity of the active state of the contractile apparatus. The toxicity of digitalis include atrioventricular junctional rhythm, premature ventricular depolarizations, bigeminal rhythm and atrioventricular blockade et al.

As mentioned above, so far there still is lacking any effective and safety drug which would treat and prevent cardiovascular disease and at the same time without any side-effect.

In addition, *Pueraria lobata* (willd) ohwi, *Salvia miltiorrhiza* Bunge, *Ligusticum chuanxion* Hort, *Ligusticum wallichii* Franch and *Codonopsis pilosula* Nannf as natural herbs used in clinic for treating and preventing cardiovascular disease.

| Reference | | | |
|---|---|---|---|
| (1) | Chinese Traditional and Herbal drugs | 2:34 | 1975: |
| (2) | Chinese Journal of Medicine | 53:591 | 1973: |
|  | Chinese Journal of Medicine | 56:689 | 1976: |
| (3) | Cardiovascular Disease | 1:1 | 1974: |
|  | Cardiovascular Disease | 1:5 | 1974: |
| (4) | Chinese Journal of Internal Medicine | 4:203 | 1977: |
| (5) | Peking Pharmaceutical Industry | 1:23 | 1976. |

SUMMARY OF THE INVENTION

It is an object of the present invention to provide a pharmaceutical compound which is safe and highly effective for treating and preventing cardiovascular disease.

These objects and other objects will become apparent hereinafter after reading the detailed description in conjunction with the examples, the present invention resides, briefly stated in compositions comprising a mixture of the following active ingredients:

(1) Puerarin and derivate puerarin were extracted from *Pueraria lobata* (willd) ohwi or *Pueraria thomsanii* Benth;

(2) Danshensu and Danshenketone were extracted from *Salvia miltiorrhiza* Bunge, *Salvia przewalskill* Maxim or *Salvia trijuga* Diels;

(3) Tetramethyl pyrazine was extracted from *Ligusticum chuanxiong* Hort or *Ligusticum wallichii* Franch;

(4) Polysaccharides and saponin of Dangshen were extracted from *Codonopsis pilosula* Nannf, *Codonopsis tangshen* Oliver or *Codonopsis clematidea* Clarke.

For the sake of convenience, compositions comprising mixtures of the above extracts will hereinafter be referred to as "PTC".

DETAILED DESCRIPTION

The present invention provides a pharmacologically effective substance (PTC) and process for isolating it. The PTC has an excellent cardiovascular effect especially in reducing myocardial oxygen demand and increasing coronary effects. The treatment of angina and other manifestations of myocardial ischemia is based on reduction of myocardial oxygen demand and increase of coronary blood flow to the ischemia myocardium to restore the balance between myocardial oxygen supply and demand. Until PTC has been invented, there is no any drug which can reduce myocardial oxygen demand and simultaneously increase of coronary blood flow. Meanwhile PTC is safe drug or health food, other cardivascular drugs have a certain degree side effect as mentioned above.

PTC can be administered to patients in the form of capsules containing a powdered mixture of the active ingredients in appropriate proportions. Alternatively, tablets can be prepared comprising the active ingredients and pharmaceutically acceptable binders, excipients, lubricants, sweeteners and coatings. A syrup or elixir may be prepared by dissolving PTC in alcohol and water together with suitable preservatives, sweeteners, dyes and flavoring agents. Ampules or vials for injection may likewise be prepared, with the PTC as prepared for oral administration being purified through further recrystallization and sterilization and the addition thereto of distilled water and other suitable solvents and additives known in the pharmaceutical art.

The PTC dosage units prepared according to the invention can be administered to patients. PTC is non-toxic.

The compositions of the present invention all include as their active component PTC, which as indicated previously, consists of a mixture of five plant extracts:
1. Puerarin or Derivate of puerarin;
2. Danshensu or Danshenketone;
3. Tetramethyl pyrazine;
4. Polysaccharides and
5. Saponin of Dangshen.

Puerarin has the following strustural formula:

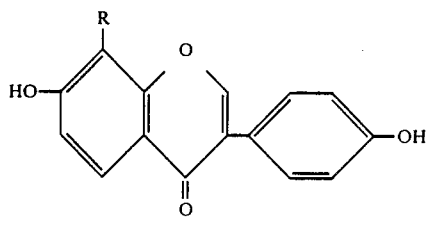

R = Glucose

Tetramethy pyrazine has the following structural formula:

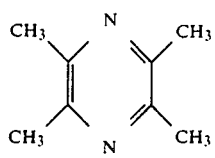

Danshensu has the following structural formula:

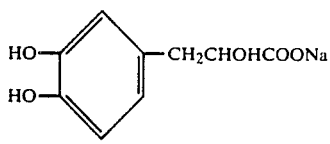

Danshenketone has the following structural formla:

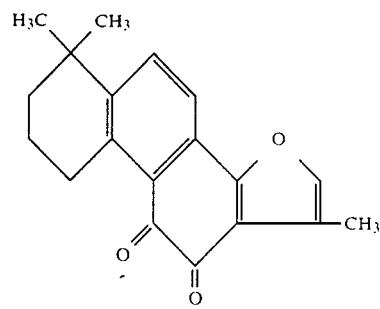

The following specific examples will provide detailed illustrations of methods of producing PTC according to the present invention and pharmaceutical dosage units containing PTC. Moreover, examples will be given of pharmaceutical testing performed with PTC which demonstrates its effectiveness in cardiovascular effects. These examples are not intended, however, to limit or restrict the scope of the invention in any way, and should not be construed as providing conditions, parameters, reagents, or starting materials which must be utilized exclusively in order to practice the present invention.

EXAMPLE 1

Extraction of Puerarin

Puerarin was extracted from *Pueraria lobata* (willd.) Ohwi or *Pueraria thomsanii* Benth.

The roots of *Pueratia lobata* (willd.) Ohwi or *Pueraria thomsanii* Benth dried and powdered. One kilogram (1 kg) of powder was dipped in 5 liters 95% ethanol. The extraction was repeated twice with fresh 95% ethanol. Extract combined. Extract was concentrated to syrup under reduced pressure and ethanol was recovered. Syrup dry at 70° C. Drying-syrup was chromatographed on alumina using water-saturated butanol as the developing solvent to separate into ten color bands which was seen under ultraviolet light (U.V.). Then using butanol-Pyridine as the developing solvent systems. From the fifth band (from the bottom) colorless columnar crystals, m.p. 187° C., were obtained after recrystallization from 50% ethánol. The final product was Pueratin and derivatives thereof.

EXAMPLE 2

Extraction of Danshensu and Danshenketone

Danshensu and Danshenketone were extracted from *Salvia miltiorrhiza* Bunge, *Salvia przewalskii* Maxim or *Salvia trijuga* Diels.

A. Extraction of Danshensu

The roots of *Salvia miltiorrhiza* Bunge dried and powdered.

10 liter of water was added to 1 kg of dry powder. The solution was heated to boil and simmered for one or one-half hours after boiling. This water extraction was repeated once and the two extracts combined and filtered. The filtrate was concentrated under reduced pressure to approximately 300 ml and 2,000 ml 95% ethanol was added with constant stirring to a final ethanol concentration of 75%. Clear solution of ethanol was withdrew. Clear solution of ethanol and the residue saved. 2,000 ml 90% ethanol was added to residue with stir. The extraction was repeated twice by collecting the ethanol, replacing it with an equal volume of fresh 90% ethanol. Ethanol was combined with clear solution of ethanol and distilled to 200 ml under reduced pressure. 200 ml water added to 200 ml ethanol solution with stir and distilled to 200 ml under reduced pressure. Alternate extraction was repeated with water and ethanol. Final solution concentrated to 85 ml under reduced pressure. The concentrated solution was allowed to stand at 4° C. Colorless needle crystals, m.p.198°-200° C., were obtained. Crystals washed with diethyl ether. Final product was danshensu.

B. Extraction of Danshenkitone 5 liter of 95% ethanol was added to 1 kg of dry powder in a water bath at 50° C. for 6 hours. The extraction was repeated twice by collecting the alcohol, replacing it with an equal volume of fresh 95% ethanol and refluxing it with an equal volume of fresh 95% ethanol for 6 hours. The extraction of ethanol was cooled and filtered. The filtrate combined with the extract filtrate. Ethanol was then recovered by reduced pressure distillation and residue obtained. 1,000 ml of benzene was added to the residue and refluxing in water bath of 50° C. for 6 hours. Benzene was concentrated under reduced pressure. Residue was chro matographed on alumina using benzene as the developing solvent to separate into violet, orange and dark-red color bands. Violet-band was cuted and continuously chromatographed using benzene as the developing solvent. Benzene was collected and concentrated under reduced pressure. Dark-red crystals were obtained and mother solution was concentrated continuously. Red-needles were crystallized. Red-needles, m.p. 202°-204° C., were obtained after recrystallization from ethanol. The red-needles were Daidzeiketone.

EXAMPLE 3

Extraction of Tetramethyl Pyrazine

Tetramethyl pyrazine was extracted from *Ligusticum chuanxiong* Hort or *Ligusticum wallichii* Franch.

2,000 ml of 95% ethanol was added to 1,000 g of powdered root and stem of as mentioned above plants and refluxed in a water bath for 2 hours. The extraction was repeated twice with fresh ethanol and further refluxing. The ethanol was recovered by concentration under reduced pressure. The residue was dissolved in warm water, cooled to room temperature and extracted twice with equal volumes of petroleum ether. The ether phase was then extracted with an equal volume of 1N HCl. The sodium carbonate was added to the water phase until its pH was 9-10, and the water phase was then extracted with an equal volume of chloroform. The chloroform phase was collected and chloroform recovered under reduced pressure. The residue gel was dissolved in petroleum ether. The ether was evaporated under reduced pressure and the residue dissolved in a mixture of petroleum ether and chloroform (8:2). The solvent was then evaporated under reduced pressure and the solid residue dissolved in warm water. The solution was cooled to room temperature and the pH adjusted to 8-9 with saturated NaOH. After distillation and cooling, needle crystals formed which were then dissolved in warm water and filtered. The product was recrystallized once by repeating the above procedure. The final tetramethyl pyrazine product was dried under vacuum and was found to have a melting point of 87.5°-88.8°C.

EXAMPLE 4

Extraction of Polysaccharides and Saponin or dangshen

A. Polysaccharides of dangshen was extracted from the roots of *Codonopsis pilosula* Nannf.

The roots of Codonopsis pilosula Nannf dried and powdered.

2,000 ml of 95% ethanol was added to 1 kg of dried powder and allowed to stand for one day at room temperature. The solution was filtered and the extract filtrate saved. 2,000 ml of ethanol was added to the residue and refluxed in a water bath for 6 hours. The refluxing was repeated twice by collecting the ethanol, replacing in with an equal volume of fresh 95% ethanol and refluxing for 6 hours. The refluxed ethanol was collected and filtered. The filtrate combined with the extract filtrate.

For the sake of convenience, solution comprising mixtures of the above filtrate and extract filtrate will hereinafter be refereed to as solution (1). The solution (1) was used for extraction of Saponin of dangshen. The residue of all process combined for extraction of polysaccharides. Residue was grind. 3,000 ml of water was added to the residue. The solution was heated to boil and simmered for 3 hours after boiling. Filtered. Cooled. Precipitated. The White precipitate was discarded. The supernatant (1) solution was collected. Centrifugaltion (approximately 1,000 rpm) carefully collect supernatant layer (2). The two volumes of fresh 95% ethanol was added to supernatant layer (2). The ethanol was recovered by distillation under reduced pressure. The residue was dissolved in warm water. Cooled to room temperature. The two volumes of fresh 95% ethanol was added to cooled solution. The precipitate was collected. The product was dried by vacuum, and the resulting powder was polysaccharides of dangshen.

B. Extraction of Saponin of dangshen:

The solution (1) was used for extraction of saponin of dangshen. Solution (1) was then recovered by reduced pressure distillation and the residue dissolved in 300 ml of distilled water. The lipid component of water solution was removed with 5 changes of 1,000 ml Diethyl ether to water solution for extraction. An equal volume of water-saturated butanol was added to the final water phase and the butanol was then distilled under reduced pressure. The residue powder was dissolved in 300 ml of ethanol and 2,000 ml of acetone was added to the ethanol with constant stirring while a precipitate formed. The precipitate was washed twice each with acetone and other with ether and dried under vacuum. The resulting white or light yellow powder was the final product, i.e., saponin of dangshen.

EXAMPLE 5

Preparation of Fine Product of PTC

Fine PTC prepared according to the present invention consists of:

|  | weight percent | preferred weight percent |
| --- | --- | --- |
| Puerarin | 10-50% | 25% |
| Dansheniu or Danshenketone | 10-50% | 25% |
| Tetramethyl Pyrazine | 10-50% | 25% |
| Polysaccharides of Dangshen | 5-25% | 12.5% |

-continued

|  | weight percent | preferred weight percent |
|---|---|---|
| Saponin of Dangshed | 5-25% | 12.5% |

The dry ingredients or derivate of ingredients prepared in accordance with the present invention, may be incorporated tablets, capsules, syrups or other form by conventional methods.

EXAMPLE 6

Preparation of Crude Product of PTC

Crude PHP is extracted from as mentioned above plants by ethanol.

Proportion of plants, for example, is as following (by weight):

|  | weight percent | preferred weight precent |
|---|---|---|
| Pueraria lobata (willd.) Ohwi or Pueraria thomsanii Benth: | 10-50% | 25% |
| Salvia miltiorrhiza Bunge, Salvia przewalskii Maxim or Salvia trijuga Diels: | 10-50% | 25% |
| Ligusticum chuanxion Hort or Ligusticum wallichii Franch: | 10-50% | 25% |
| Codonopsis pilosula Nannf, Codonopsis tangshen Oliver or Codonopsis clematidea Clarke: | 10-50% | 25% |

Tissues of plant were dried and powdered. 5 liter distillatory water was added 1 kg of dried powder. The solution was heated to boil and simmered for one hour after boiling. This water extraction was repeated two times. Combined and filtered. The filtrate was concentrated under reduced pressure to approximately 500 ml. Then 1,000 ml 95% ethanol was added to 500 ml water solution. Stirred. Stilled. Filtered. Residue and filtrat (A) was obtained. 1,000 ml 90% ethanol was added to residue. Stirred. Extracted. 90% ethanol extraction was repeated two times. Extraction of 90% ethanol was combined. Filtered. Filtrate (B) was obtained. Combined filtrate (A) with (B). Then total filtrate was concentrated to syrup under reduced pressure distillation. Ethanol was recovered. Syrup dried under vacuum drying. Granulated to final powder. Weight of every capsule and table is about 100-200 mg. Crude-PTC is similar to fine-PTC in pharmacological property.

The following examples are related to pharmacological test:

EXAMPLE 7

Effect of PTC on Coronary Flow

Male rats (280 to 320 g body weight), maintained on a standard diet, were used in these experiment. The rats were lightly anaesthetized with diethyl ether. The left femoral vein was exposed and heparin (200 IU) was administered intravenously. One minute (min) after administration of heparin, the heart was excised and placed in ice cold perfusion medium until contraction had ceased. The heart was then mounted on the perfusion apparatus. Bicarbonate (PH 7.4) buffer was the standard perfusion fluid. The perfusion fluid was maintained at 37° C. and in aerobic studies, the fluid was equilibrated with $O_2 + CO_2$ (95:5). Aortic $O_2$ Partial pressure was over 600 mm Hg. The heart was perfused after mounting immediately for a 5 min wash-out period. The preparation was then converted into working heart system for a 15 min period (standard perfusion medium plus 11 mM glucose). Flow meter calibrate for flow (5 to 70 ml/min) at 37° C. was used to measure aortic flow rates. The drug was included separately in perfusion medium thoughout the experimental time course.

Statistical comparison between control and PTC group was made by Student's T-test with the significance level being $P < 0.05$. Values given are means ± standard error (S.E.M.).

The experimental results are listed in the following table:

TABLE 1

|  |  | Coronary flow (ml/min) | Number of Samples |
|---|---|---|---|
| Pretreatment |  | 6.7 ± 0.6 | 10 |
| After treatment of PTC (min) | 1' | 10.6 ± 0.9 | 10 |
|  | 3' | 10.4 ± 0.8 | 10 |
|  | 5' | 0.3 ± 0.9 | 10 |
|  | 10' | 6.9 ± 0.5 | 10 |
|  | 15' | 6.7 ± 0.4 | 10 |
|  | 20' | 6.7 ± 0.5 | 10 |
| p |  | <0.01 |  |

EXAMPLE 8

The Effect of PTC on Myocardial Nutrious Blood Flow in Mice

In the present example the effect of the myocardial uptake of $^{86}Rb$ (Rubidium) used as the index of myocardial nutrious blood flow. The male mice weight 18-22 g were used in the experiments and were divided into treated (PTC) and control group. The dosage of PTC was 50 mg/kg injected intraperitoneally. The control mice were injected with same volume of normal saline. These injections were repeated daily for four days. On the last day, both PTC and control group $^{86}Rb$ 50 μ/kg body weight was administered by tail vein, the injections to be completed within 3 seconds for every mouse. 30 seconds after administration of $^{86}Rb$ the heart was excised. The heart was then dissected and weighted after the removal of auricles and blotted with filter paper quickly. The heart was digested by 1.25N NaOH in a boiled water bath. Then dry digested solution with infrared drier. The $^{86}Rb$ uptakes were determined on a scintillator. The coronary blood flow was expressed as the per minute per gram heart weight in pulse to amount of $^{86}Rb$ given (CPM/g).

The experimental results are listed in the following table:

TABLE 2

|  | Control | PDC |
|---|---|---|
| CPM/g | 138.0 ± 10 | 212.5 ± 11.6 |
| Number of sample | 20 | 20 |
| p |  | <0.01 |

EXAMPLE 9

Effect of PTC of Lactate Levels in Heart Tissue

The male rats (280 to 320 g body weight) maintaine on a standard diet, were used in these experiments. The rats were lightly anacethetized with diethyl ether, the left femoral vein was exposed and heparin (200 IU) was administered intravenously. 1 minute after administration of hepairin the heart was excised and placed in ice cold perfusion medium until contraction had ceased. The heart was then mounted on the perfusion apparatus. Left atrial filling pressure was maintained at 7.5 mm Hg and aortic resistance was maintained by 70 mm Hg in aortic outflow tract.

Langendorff perfusion for an initial 10 min period, the perfusion was continued as a working preparation for an additional 30 min. The hearts were all electrically paced at between 265 and 275 beats/min during working perfusion. This work load resulted in 60% to 75% of maximal, maintainable peak systolic pressure.

The perfusate was Krebs-Henseleit bicarbonate buffer gassed with 95% oxygen and 5% carbon dioxide. This perfusate contained 11 mM D-glucose during the Langendorff perfusion, and 11 mM D-glucose plus 1.4 mM palmitate bound to 3% bovine serum albumin.

Aortic pressure, heart rates, coronary flows and aortic outputs were monitored during perfusion. At the end of the perfusion period, the hearts were frozen cooled to the temperature of liquid nitrogen, while still being perfused. The frozen hearts were stored in liquid nitrogen until assayed for metabolic intermediates.

The tissue sample was extracted in ice-cold 10% trichloroacetic acid and centrifuged at 10,000×g for 15 min at 4° C. The precipitates of trichloroacetic acid were washed with 1% trichloroacetic acid and subsequently used for determining levels of lactate. The data were expressed per gram of non-collagen protein (NCP). Chemical colorimetric methods had been used in the analysis of lactate levels in heart tissue.

During the anoxic perfusion period, atmospheric gas contamination of the heart was prevented by completely enclosing the heart in a waterjacketed (37° C.) chamber which was continuously gassed with a mixture of $N_2+CO_2$ (95:5). In addition, to prevent diffusion of oxygen into the perfusion fluid; all silicone rubber tubing, connecting reservoirs and the heart, was replaced by glass delivery tubing. Perfusion medium was equilibrated with $N_2+CO_2$ (95:5).

Example 9 is similar to example 7 in methods of animal. The lactate concentrations in heart of control group increased markedly, whereas lactate concentrations of PTC group did not increase. The data of lactate of PTC can be meant to reduce the degree of myocardial infarct.

The experimental results are listed in the following table:

TABLE 3

|  | Normal | Control | PTC |
| --- | --- | --- | --- |
| Number of sample | 10 | 10 | 10 |
| Lactate (mols/g NCP) | 3.2 ± 0.2 | 5.1 ± 0.3 | 3.3 ± 0.2 |
| P | — |  | <0.01 |

EXAMPLE 10

Effect of PTC on Isolated Cardiac Muscles

Adult male guineapigs (300–450 g), maintained on a standard diet, were used in these experiments. The guineapigs were lightly anaesthetized with diethyl ether, then each guineapig was killed by a sharp blow on the head and blod out, the heart was excised immediately and placed in dish containing oxygenated Krebs-Henseleit solution at 29° C.

Krebs-Henseleit solution has the following materials (millimolar/liter):

| | |
| --- | --- |
| NaCl | 118 |
| $NaHCO_3$ | 25 |
| $CaCl_2$ | 2.52 |
| KCl | 4.7 |
| $MgCl_2$ | 1.2 |
| $NaH_2PO_4$ | 1.18 |
| Glucose | 5.55 |

Intact right and left atria was dissected out in a piece, free from ventricular and connective tissues, maintained on a Krebe-Henseleit solution at 32° C. Krebs-Henseleit solution was equilibrated with 5% $CO_2+95\%$ $O_2$ gas mixture. Isolated cardiac muscles were subjected to a resting tension of 0.75 g and left to equilibrate in the bath until the rate and amplitude of spontaneous contractions were stable. Then isolated cardiac muscles were treated with PTC, PTC was administered to the bath fluid in a cumulative manner. The cardiac muscles were treated with PTC repeatedly at intervals of 20 minutes after the last washing. The spontaneous amplitude and rate of contractions as well as the PTC evoked responses of cardiac muscles were recorded isometrically by mean of devices forcedisplacement transducers, preamplifier and two-channel heat sensitive pen recorder. PTC was determined at a paper speed of 10 mm Sec.

The experimental results are listed in the following table:

TABLE 4

| | Inhibined percent age % | | |
| --- | --- | --- | --- |
| | Rate of contractions | Chronotropic responses | Inotropic responses |
| 80 µl/ml | 54.9% | 49.0% | 38.7% |
| P | <0.01 | <0.1 | <0.1 |

EXAMPLE 11

Effect of PTC on the Oxygen Consumption Rate and Survival Percentage of Mice under Hypoxia The male mice weighy 18–20 g were used in the experiments and were divided into PTC and control group. The dosage of PTC was 50 mg/kg injected intraperitoneally. The control mice were injected with same volume of normal saline. These injections were repeated daily for four days. On the last day, bath PTC and control group mice have been placed in airtight box. Oxygen of box was measured with bare-tip platinum electrode. Atmospheric pressure of airtight box was reduced to 180 mm Hg with air pump. PTC group resulted in a prolongation of survival time and elevation of survival percentage of the mice under hypoxia. In PTC group the residual content of oxygen more than the control at 16 min after reduced pressure. It illustrats that PTC might improve the oxygen utilization during hypoxia.

The experimental results are listed in the following table:

TABLE 5

| | Survival time (min) | Survival percentage (%) | Residual $O_2$ percentage in atmospheric (%) |
| --- | --- | --- | --- |
| Control | 16 ± 2 | 0 | 6.4 ± 0.4 |
| PTC | 58 ± 5 | 84 | 8.4 ± 0.5 |
| P | <0.01 | <0.001 | <0.01 |

EXAMPLE 12

Effect of PTC on Aggregation of Platelets

Methods for blood humans:

Blood was collected from veins of humans using a needle attached to a plastic disposal syringe. The blood was immediately transtered into siliconized glass tube containing 0.1 volume of 3.13% sodium citrate. Platelet-rich plasma (PRP) was obtained by centrifugation of the whole blood at 1,000 rpm for 10 min at room temperature. Platelet-poor plasma (PPP) was prepared by centrifugation of the remaining blood at 3,000 rpm for 10 min. Platelet aggregation was performed using in aggregameter at 37° C. Human platelet studies were carried out at constant platelet number ($3 \times 10^8$ /ml). With regards to determination of platelet aggregation, the maximum aggregation induced by adenosine diphosphate (ADP) in a final concentration of 2 $\mu$M was obtained by the light transmission method. 0.4 ml PRP of each subject was introduced into each of 24 tubes and divided into 2 groups. Then to the 12 tubes of each group were added 50 $\mu$l of saline and 50 $\mu$l PHP (0.5 mg/ml) respectively. After incubation of 3 min at 37° C., to each of 12 tubes of each group were added 50 $\mu$l of 2 $\mu$M ADP. A 5 min aggregation curve for each tube was plotte.

Percent inhibition of aggregation by PTC was calculated by:

$$\% \text{ inhibition of aggregation} = \frac{\% \text{ aggregation in control} - \% \text{ aggregation with PHP}}{\% \text{ aggregation in control}} \times 100$$

The experimental results are listed in the following table:

TABLE 6

|  | Rate of aggregation of platelet | Percent inhibition of aggregation |
| --- | --- | --- |
| Control | 67.5 ± 5.0 | — |
| PTO | 19.8 ± 1.5 | 70.6% |
| P | <0.01 | |

EXAMPLE 13

Effect of PTC on Immune Function (1) Animal section

1 Inject 2 ml of normal saline into the peritoneal cavity of mouse for control group and 50 mg/kg PTC for PTC group daily.

2 Kill the animal after 3 days.

3 Inject 2-5 ml of tissue culture medium into the peritoneal cavity and gently press the abdomen to bring the cells into suspension.

4 Open the abdominal skin of the mouse and hold up the centre of the peritoneum with forceps.

5 Make a small hole in the peritoneum and remove the medium with a pipe.

6 Finally open the mouse fully and suck out all the medium.

7 Estimate the number of phagocytes by the uptake of a 1% neutral red solution (haemocytometer count).

(2) Stained method

Add 0.02 ml of 5% washed chick red blood cell suspension to 0.5 ml of the peritoneal exudate, shake gently to mix and incubate at 37° C. for 5 minutes. Dip two coverslips, close to each other, in the above mixture and incubate for 30 minutes for the migration of the macrophages along the cover slips, fix and stain with sharma stain. Examine microscopically for:

Phagocytic rate—number of macrophages with phagocytized chick red blood cells per 100 macrophages counted.

Results:

Results as illustrated by the following table:

TABLE 7A

|  | Normal | PTC |
| --- | --- | --- |
| Phagocytic percent + SD(%) | 35.10 ± 2.01 | 50.4 ± 4.10 |
| Number of sample | 12 | 12 |
| P | <0.01 | |

(3) $^{53}$Cr labeling method:

Method—Counted the number of macrophages in the peritoneal exudate of mice and adjusted to $1 \times 10^7$ cell/ml with normal saline. Added 0.1 ml of the macrophage suspension i.e. $1 \times 10^6$ cells to each well on the plastic plate for the test. Labelled the chick red blood cell with $^{53}$Cr, suspend the label chick red blood cell and adjusted to $1.5 \times 10^8$/ml, added 0.1 ml, i.e. $1.5 \times 10^7$, to each well. Incubated at 37° C. for 30 min., washed to remove the free chick red blood cells. Counted each well in a $\gamma$-counter.

The results are listed below tabel.

TABLE 7B

|  | Normal | PTC |
| --- | --- | --- |
| CPM | 1089 ± 341 | 3041 ± 401 |
| Number of sample | 12 | 12 |
| P | <0.0001 | |

The above data of phagocytosis illustrated that PTC can increase immune function in mice.

EXAMPLE 14

Effect of PTC on Oxygen Uptake of Rat Heart

The male rats (280 to 320 g body weight) were killed by decapitation and the hearts were immediately removed, opened, and washed in cold M/30 phosphate buffer. The buffer was M/30 potassium phosphate and was adjusted to pH 7.4. The hearts then were homogenized in cold buffer containing one of the following substrates, depending upon the experiment being performed: glucose or pyruvate. The homogenates were prepared so that 1 cc. contained 100 mg of fresh tissue. One cubic centimeter of homogenate was added to iced Warburg vessels containing 1.3 cc. of buffer in the main compartment, 0.5 cc. of 100 $\mu$M PTC or buffer in the sidearm, and 0.2 cc. of 10% KOH plus a pleated strip of No.41 filter paper in the center well. The gas phase was air and the temperature of the bath was 37° C. After a ten-minute equilibration period the sidearm contents were tipped into the main compartment, the manometers were closed and the oxygen consumption was read after one hour. The pH of all solution was adjusted to 7.4 before use. For each experiment eight rats were used and several flasks were run simultaneously with homogenate from each rat. The experimental results are listed in the following Table 8.

TABLE 8

| | concentration of substrate | | | | | |
|---|---|---|---|---|---|---|
| | None | | 0.011M glucose | | 0.015M pyruvate | |
| | Control | PTC | Control | PTC | Control | PTC |
| Oxygen uptake | 30 ± 2.7 | 19.5 ± 1.0 | 45 ± 3.0 | 31.5 ± 2.5 | 160± 11 | 96 ± 8.1 |
| Number sample | 8 | 8 | 8 | 8 | 8 | 8 |
| P | <0.01 | | <0.1 | | <0.001 | |

EXAMPLE 15

Safety of PTC

10% solution of PTC was administered intraperitoneally in mice. No reactions were observed. The acute $LD_{50}$ was found to be 918 mg/kg. Each dose for an adult is 50 mg. Using 50 kg as the average weight of an adult the dosage is 1 mg/kg, therefore it is very safe.

It will thus be shown that there are provided compositions and methods which achieve the various objects of the invention, and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the appended claims:

1. A process for producing Danshensu comprising:
   a. extracting ground roots of a plant selected from the group consisting of *Salvia miltiorrhiza* Bunge, *Salvia przewalskii* Maxim and *Salvia trijuga* Diels with boiling water;
   b. concentrating the aqueous extract under reduced pressure;
   c. adding a sufficent amount of 95% ethanol to the concentrated extract to form an extract containing 75% of ethanol and collecting the ethanol extract;
   d. concentrating the ethanol extract under reduced pressure to yield a residue;
   e. alternately extracting the residue of step d with an equal amount of water and then with an equal amount of ethanol;
   f. concentrating the resulting combined extracts of step e under reduced pressure; and
   g. crystallizing Danshensu at 4 degrees C.

2. The process of claim 1 further comprising washing Danshensu with diethyl ether.

3. A process for producing Danshenketone comprising:
   a. extracting ground roots of a plant selected from the group consisting of *Salvia miltiorrhiza* Bunge, *Salvia przewalskii* Maxim and *Salvia trijuga* Diels with 95% ethanol at 50 degrees C.;
   b. concentrating the ethanol extract under reduced pressure to yield a residue;
   c. extracting the residue with benzene;
   d. concentrating the resulting benzene extract under reduced pressure;
   e. chromatographing the concentrated benzene extract on alumina and developing three colored bands of violet, orange and dark-red with benzene;
   f. eluting the dark-red band with benzene;
   g. concentrating the resulting benzene solution; and
   h. crystallizing the Danshenketone as red needles.

4. The process of 3 further comprising the step of washing said needles with ethanol and drying the same under vacuum.

* * * * *

UNITED STATES PATENT AND TRADEMARK OFFICE
CERTIFICATE OF CORRECTION

PATENT NO. : 4,999,376
DATED : March 12, 1991
INVENTOR(S) : Yaguang Liu

It is certified that error appears in the above-identified patent and that said Letters Patent is hereby corrected as shown below:

On the title page, item [54] and column 1, in the title "CARDIOVASULAR" should read—CARDIOVASCULAR--.

Signed and Sealed this

Fifth Day of May, 1998

*Attest:*

BRUCE LEHMAN

*Attesting Officer*   *Commissioner of Patents and Trademarks*